United States Patent [19]
Von Berg

[11] Patent Number: 4,953,594
[45] Date of Patent: Sep. 4, 1990

[54] FLOW CONTROL

[75] Inventor: Peter Von Berg, Neukeferloh, Fed. Rep. of Germany

[73] Assignee: Peter Von Berg Extrakorporale Systeme Medizintechnik, Kirchseeon/Eglharting, Fed. Rep. of Germany

[21] Appl. No.: 165,951

[22] Filed: Nov. 25, 1987

[30] Foreign Application Priority Data

| Aug. 20, 1987 [DE] | Fed. Rep. of Germany | 3727816 |
| Jan. 9, 1987 [DE] | Fed. Rep. of Germany | 3700502 |
| Dec. 15, 1986 [JP] | Japan | 3642182 |

[51] Int. Cl.$^5$ .............................................. A61M 5/005
[52] U.S. Cl. .............................. 137/614.18; 251/126; 251/291; 604/249
[58] Field of Search ............... 251/291, 126, 904, 4, 251/7, 273; 137/614.18, 613; 604/246, 249

[56] References Cited

U.S. PATENT DOCUMENTS

| 1,763,687 | 6/1930 | Chadwick et al. | 251/126 |
| 3,503,586 | 3/1970 | Bordes | 251/291 |
| 4,361,147 | 11/1982 | Aslanian et al. | 604/249 |
| 4,434,963 | 3/1984 | Russell | 251/7 |
| 4,632,359 | 12/1986 | Tooth | 251/126 |
| 4,634,434 | 1/1987 | Marino, Jr. et al. | 251/126 |
| 4,673,161 | 6/1987 | Flynn et al. | 251/7 |

FOREIGN PATENT DOCUMENTS

894360  4/1962  United Kingdom ............... 251/126

Primary Examiner—A. Michael Chambers
Attorney, Agent, or Firm—Helfgott & Karas

[57] ABSTRACT

A metering device for adjusting a flow rate of a flow of liquid comprises a flow-rate adjusting device including a rotatable adjusting member, and an actuating member for rotating the adjusting member. The actuating member is connectable with the adjusting member and may be disengaged therefrom in a respective adjusted position in order to avoid unintentional or incomplete adjustment of the metering device. A hexagonal head and a mating hexagonal recess are provided on either the adjusting member or the actuating member to effect engaging and disengaging of these members.

13 Claims, 5 Drawing Sheets

FLOW CONTROL

BACKGROUND OF THE INVENTION

A metering means for adjusting the flow rate of a liquid flow into and out of the body of a living being.

The invention relates to a metering device for adjusting the flow rate of a liquid flow directed into and out of the body of a living being in a flow passage, for example for parenteral or intravenous infusion. An adjusting means operable by an actuating member is provided to vary the flow resistance of the flow passage. The members of adjustment of the adjusting means are guarded against unintentional or intentional adjustment by a locking means.

SUMMARY OF THE INVENTION

It is the object of the invention to realize this locking means such that its manufacturing technique is simple.

This object is met, in accordance with the invention, in that the locking means in the metering device of the kind specified initially is constituted substantially by the actuating member and the adjusting means and, to this end as well as for their mutual releasable engagement, both these parts are adapted to each other in the manner of a key and lock system.

This solution has the advantage that no other structural elements must be produced for guarding purposes but those which must be made anyhow, namely the adjusting means and its actuating member.

In addition, the metering device according to the invention provides an increased safety effect as compared, for instance, to the device known from DE 35 90 339 T1. By virtue of the mutual adaptation of the adjusting means and the actuating members in the manner of a system of lock and key, the adjusting means can be influenced only by the actuating member. The setting of the adjusting members cannot be changed once the hospital staff has pulled out the actuating member like a key from its lock.

In accordance with a preferred embodiment, the adjusting means is designed like a valve, in other words it comprises a valve housing through which extends the flow passage and a valve body which is guided for movement inside the same to vary the flow resistance (cross section and/or length of the flow passage). The end of the actuating member remote from the flow passage is adapted for releasable engagement in the manner of a lock and key system. In this manner, the disadvantages of a known squeeze roller metering means are avoided and, at the same time, convenient mutual engagement is warranted between the actuating member and the adjusting means. Preferably, the valve body is guided by a thread inside the housing and the actuating member is embodied by a rotatable knob.

The thread also may serve as flow passage, especially so if it is formed as a trapezoidal thread.

In a particularly simple embodiment the valve body and the actuating member provided for the same are adapted to each other for mutual snapping engagement and/or mutual hexagon (polygonal) socket-type engagement such as known per se and approved with two parts which are to be connected releasably. The snap connection permits the valve body to be displaced inside the housing not only by way of rotation about the axis but also directly in axial direction.

Additionally, the rotary knob presenting the actuating member preferably has a cylindrical recess at one side with a first axle journal protruding coaxially from the bottom thereof for engagement with the valve body. It is preferred if the length of this axle journal is somewhat smaller than the depth of the recess and, moreover, preferably a second axle journal protrudes from the other side of the rotary knob and is designed for the same engagement with the valve body as the first axle journal.

The valve housing and valve body preferably are adapted to each other such that the valve body remains inside the valve housing during any movement needed to vary the flow resistance.

Preferably, at least the end portion of the valve housing remote from the flow passage is made of an elastically deformable material and cylindrical in shape, the free edge of the end portion of the housing and the free edge of the recess in the rotary knob each comprising an annular bead and the diameters of the beads being so selected that the end portion of the housing, when introduced, snaps into the recess in the rotary knob.

The interior wall of the valve housing and/or the exterior wall of the valve body preferably are formed like threads in that area in which the two connecting pieces of the valve housing are offset with respect to each other, the thread being made such that the course of the thread functions as the flow passage whose axial length is variable by axial displacement of the valve body in the valve housing.

With this design of the valve, the attending physician may carry along the actuating member which is suitable for adjustment of all existing valves, in the manner of a master key, while the nursing staff carries only actuating members which are suitable exclusively for operating the metering valves under their care.

It is another object of the invention to develop this valve such that it can be operated easily and accurately by one hand or connected thus to a separate adjustment drive, without sacrificing the advantages described above.

A handle or a torque support for a separate adjustment drive means in this case is mounted on or formed integrally with the valve housing, in accordance with the invention. It is likewise conceivable that a supporting element of the separate adjustment drive embraces the handle, for instance, like a fork so that the handle likewise may serve as torque support, if desired.

At any rate, if a person sets the metering valve, one hand always remains free for some other task, such as operating a blood pressure measuring instrument or holding a stethoscope.

The handle can be mounted on the valve housing in such manner that the thumb and forefinger of the hand can reach the handling portion of the actuating member rather comfortably, while the other three fingers of the same hand grip the handle. If the actuating member, however, is slipped on loosely only, there may be a risk that the actuating member becomes disengaged from the actuating connection during operation because of the ergonomically unfavorable positioning of the operator's thumb and forefinger if the metering valve is badly accomplished. To avoid that, a preferred modification of the invention provides for the valve body, the actuating mechanism, and/or the actuating member to be so designed that the handle thereof is located at such a distance from the handle at the valve body that the operator can manipulate it with his or her thumb and forefinger without any effort. In this manner not only very sensitive adjustment of the metering valve is permitted but also the inadvertent disengagement of the actuating member from the actuating connection during the setting is prevented reliably.

A separate handle preferably of anatomical design could be mounted on the valve housing. Yet this would make the arrangement rather heavy. For this reason it is preferred to have the extended inlet or outlet nozzle act as handle or torque support. That is totally sufficient as handle in spite of the usually quite small diameter thereof, all the more so in view of the fact that normally only little force is required to operate the actuating member. The valve thus modified is very light and, therefore, can be disposed freely in a suspended infusion tube, without compromising the reliability of the tube connections of the valve.

The valve housing may be made of any material which permits simple manufacture, such as pressure molding of plastics and which is sufficiently inert to the liquid to be metered. Transparent material is preferred and even more preferred is a colorless material so that the beginning and termination of flow and partly even the flow rate can be observed. Thus the accurate adjustment of the valve is supported visually, and this makes it possible to set the same sufficiently sensitively even by that hand which usually is not the preferred one, normally the left hand.

It is preferred to have the valve body or the part of the actuating mechanism which is moved together with the same distinguished by color, either totally or at least in the area of a mark, especially a graduation so that it or the mark can be recognized at once from the outside. With one-handed manipulation, alternatingly using the left or right hand to operate the actuating member it is easy to confuse the direction of rotation. Yet with the modification mentioned, the direct observation of the mark or of the valve body or the actuating mechanism makes it possible to realize at once whether or not the setting takes place in the right direction.

It is likewise conceivable to provide an optical observation means at the outside of the valve housing and at the valve body, the actuating mechanism, or opposite a mark to determine the extent of adjusting movement. For instance, if the valve is connected to a separate adjustment drive means by way of a flexible drive transmission, the adjustment distance, such as the number of revolutions taken by the drive means is not always representative of the adjustment distance which the valve body passes.

Furthermore, it is possible to allocate an adjustment value gained from experience to the flow rate of each liquid metered, in response to the viscosity thereof. This value either is set directly during manual handling of the metering valve according to the invention or entered into the control of an adjusting servo drive means as the first rated value. In this manner the time required for setting the metering valve becomes even shorter.

In accordance with another preferred modification of the invention a means is provided in the metering valve, specifically in the valve body, the valve chamber, or the discharge nozzle to cause the dripping of the metered liquid. In this case the response behavior of the metering valve to the respective setting made can be monitored especially quickly and this in turn permits even more accurate and rapid adjustment of the desired flow rate.

The length of the discharge nozzle which preferably presents the handle in this case is extended so that the point from which the liquid drops will not be covered by the hand holding the metering valve.

Finally, the transparent character of the metering valve also permits use of an optically effective observation means to detect the flow rate, particularly the dripping rate. Preferably, the observation means is connected at its output end to a monitoring means or to the control of the servo drive means and it responds in case of a given difference by which the actual value of the flow rate or number of drops deviates from the rated value, for instance in case of disturbance by the clogging of the valve chamber in spite of the metering valve being open Such a monitoring means may be embodied by a light barrier or drop counter.

The actuating connection of the valve mentioned initially is formed as a hexagonal recess. Yet it is possible as well to give the actuating connection the general configuration of a non-circular pin, preferably a tetragonal or hexagonal pin. It is a special advantage of this modification that simply a hose slipped on the non-circular pin may be used as flexible shaft for connection of a separate servo motor to balance errors in the alignment between the output shaft of that drive means and the actuating connection. The actuating member is formed with an analogous non-circular bore, preferably being a through bore. The purpose hereof is not only to avoid the inclusion of air when pushing the actuating member on the non-circular pin but also to permit the connection of a drive means the output shaft of which is embodied by a non-circular pin of the same nature as the actuating connection.

The link thus established between the actuating connection and the adjustment drive is almost free of torsion so that a measuring magnitude from the drive means, such as the number of revolutions accomplished may be used for control of the adjusting motion of the valve body. To this end the drive means preferably comprises a self-locking gear which does not permit rotation of the output shaft of the drive means and thus of the actuating member and its handle as well unless this rotation is caused by the drive means itself. Unauthorized manual regulation of the drive means is impossible in this case.

If a hose is used as flexible shaft, the actuating member is dispensed with. In this case, too, any readjustment of the valve by unauthorized persons practically is excluded because there is no actuating member whose manipulating portion could be recognized as suitable for setting the metering valve.

If a threaded arrangement is provided as the actuating mechanism, it is possible, in principle, to make use of the connection of the valve body to the valve chamber as the final stop for the closing position of the valve. However, as the valve closing body and the valve chamber preferably are conical in shape, this might produce very high clamping forces which even might lead to bursting of the valve chamber. For this reason, the threaded arrangement of another preferred modification of the invention is designed such that it forms a final stop when the valve body is screwed in entirely and located in its closing position. It is quite well possible that a capillary gap around the valve body still exists, yet liquid will not flow. The metering valve according to the invention normally is exposed only to a minor pressure gradient of 1 m water column (hydrostatic head pressure) at most so that flow through the capillary gap will not take place because of the viscosity of the liquids usually applied.

In assembly, such a valve body is screwed from outside by its external thread into the internal thread of the valve housing and, therefore, it can be unscrewed in the opposite direction. In accordance with another preferred modification of the invention a final stop is provided also in the opening position of the valve body. This prevents inadvertent unscrewing of the valve body. Especially in the case of one-handed operation it may happen that, in rotating the actuating member, this at first is turned in the wrong direction until the threaded engagement is cancelled. Then no more than any careless movement will suffice to let the valve body drop from the valve housing. As a consequence the liquid to be metered would run out of the opening in which normally the actuating connection passes through the wall of the valve housing. Furthermore, air may enter through this opening into the outlet socket. These disturbances are avoided by the further development of the invention.

The travel stop in opening position of the valve body is important also when a servo motor is used: if failure of the control, always releasing alarm, should yet entail the continued operation of the drive means without interruption, this particular modification prevents the separation of the valve body from the valve housing before a control person has intervened.

In the case of the known metering valve mentioned initially the actuating member is guided for sliding movement on the valve housing. Now then, if the housing is held by one hand and the actuating member by the other, it is readily possible to effect even minute adjusting rotations in spite of the transition from static friction to sliding friction. This is not so easy with one-handed operation. Therefore, in accordance with another preferred modification of the invention a bearing body is disposed at the valve housing opposite the actuating member designed as a rotatable member or rotary knob, and the rotary knob is guided by and thus in frictional engagement with the bearing body. This bearing body is made of a material which, in being paired with the material of the rotary knob, has such a low coefficient of friction that the shock which occurs upon transition from static to sliding friction is extremely small only. Consequently it is readily possible to adjust the rotary knob by no more than a minute angle of rotation, even with one-handed manipulation. The material of the bearing body preferably is self-lubricating plastic or a plastic material which exhibits a very low coefficient of friction with respect to other materials.

Those skilled in the art are familiar with such substances and, therefore, in a position to select them readily so as to meet specific requirements.

The bearing body also may be presented by a coating applied on the valve housing and/or the actuating member in the area of the frictional engagement.

Preferably, the bearing body is embodied by a bearing bush or sleeve introduced from outside into that aperture of the valve housing through which passes the actuating connection. The bearing sleeve includes an inwardly directed flange through which the actuating connection extends rotatably.

If the actuating connection is embodied by a non-circular pin in accordance with the preferred embodiment mentioned, then the actuating member includes a corresponding receiving sleeve which is adapted to be slipped on the pin and then is guided at its outside periphery in the bearing sleeve. This arrangement, at the same time, permits easy adjusting movements of the actuating member and facilitates the mounting of the actuating member on the actuating connection. These two elements both are centered by the bearing sleeve. And they are harmonized and dimensioned with respect to each other such that engagement is effected between the bearing sleeve and the actuating member before the latter engages the actuating connection, when the two elements are pushed on or into each other.

The bearing sleeve may protrude towards the outside of the valve housing. The actuating member carries a serrated or fluted sealing ring, i.e. a sealing ring which is suitable for manipulation and connected by a flange with an internal sleeve concentric with the rotatable ring and adapted to be placed on the actuating connection. If this flange abuts against the end face of the bearing sleeve, the friction between these elements, too, is reduced so that on the whole the sensitive turning of the actuating connection is enhanced still further.

In accordance with another preferred modification of the invention the breakthrough in the bearing sleeve being passed by the actuating connection is given such size that it is smaller than the external thread formed on the extension of the valve body. According to the preferred modification the bearing sleeve in turn is fixed in the valve housing, preferably by bonding so as to present the end stop for the valve body in its opening position and readily prevent the valve body from being unscrewed altogether.

Many bonding agents adhere poorly to materials having excellent sliding properties, such as the material of which the bearing sleeve is made Therefore, the bearing sleeve preferably is fixed in the valve housing by an adhesive which dissolves the surface material of these two bodies so as to establish a reliable and firm connection between them.

It is likewise possible to select an adhesive which will form a firm bond with only one of these two bodies and which itself will become fully cured. The other one of the two parts mentioned in that event will be formed with undercut recesses to be filled by the adhesive during assembly. The cured adhesive also prevents those two parts from separating. The recesses mentioned also may be formed opposite each other in both parts Then the adhesive is chosen with a view to being a substance which sets sufficiently well. Again, both parts are interconnected inseparably.

The risk of gross false manipulation by unskilled or careless staff cannot be excluded altogether with the metering valve of the invention, just as with any conventional metering valve. Nor can it be excluded with absolute certainty, without great technical expenditure, that an adjusting or regulating drive means or servo motor for setting the metering valve will not fail some day such that it will make the metering valve inadmissibly wide open. Finally, it cannot be excluded entirely that the liquid flow being dispensed through the metering valve must be interrupted suddenly and unexcpectedly when the attending physician does not have the actuating member for the valve body at hand.

Such situations pose a risk in particular when drugs are administered which by no means must be given in an overdose.

For this reason it is suggested, according to another modification of the invention, to furnish the metering valve according to the invention with an additional shutoff means, especially for emergency cases so as to render the metering valve even more appropriate for one-handed use without adjustment by an outside drive means.

Such a shutoff means preferably is connected downstream of the valve body so as to prevent germs, air, or the like from penetrating into the tube leading to the patient in case the valve body should become destroyed by grossly inappropriate handling.

The shutoff means preferably may be a power-controlled check valve adapted to be controlled from outside, such as by an electromagnet. This modification has the advantage that the shutoff means may be controlled by the control of the external drive means, if need be, for example if this control determines that the external drive means which it is monitoring runs out of control.

According to the preferred modification of the invention, however, the shutoff means is designed as a hose clamp of very simple structure, including two clamping legs which are arranged like a fork and define a clamping slot between them. The width of this slot is just wide enough for the respective tube to be pushed into the slot and to be squeezed tight.

Where the metering valve according to the invention is designed for operation by hand alone, it is especially advantageous to make the shutoff means as light as possible in order not to impair the seating of the tube connections on the metering valve by too much weight of this shutoff means.

It is another advantage of the arrangement of the hose or tube clamp at the handle that the tube may be pressed into the clamping slot, if necessary, for instance by the fingers holding the handle.

To facilitate the above, the hose clamp of another preferred modification of the invention is placed at the side of the handle remote from the actuating member or molded integrally with the same and, as already mentioned, the handle may be formed as discharge socket. Furthermore, the clamping legs preferably are tapered at their free ends towards the clamping slot. Thus they provide guidance upon insertion of the tube into the clamping slot and, at the same time, a seat for the tube: In operating the metering valve according to the invention the handle is grasped by the hand while the tube itself is arranged in the seat formed at the end of the clamping legs. If the user wishes to interrupt the flow of liquid suddenly, it is sufficient to press the tube briefly against the clamping slot by the same hand which holds it together with the handle In this manner the tube is entered safely into the clamping slot and the drug supply to the patient may be shutoff at once.

It presents no problem to lift the tube out of the clamping slot by one hand, all this requires is to introduce a finger between the tube and the housing As long as the tube is placed in the clamping slot, the actuating member can be set without the risk of administering too much medicine to the patient.

The hose or tube clamp according to the invention has yet another advantage in that drug administration to the patient may be interrupted totally for a short time, such as when the fitting of the cannula must be corrected through which the medicine is infused into the patient's body, while it is not necessary at the same time to change the accurate and proper setting made of the actuating member and thus of the valve body.

BRIEF DESCRIPTION OF THE INVENTION

DETAILED DESCRIPTION OF THE PREFERRED EMBODIMENT

Figure 1:
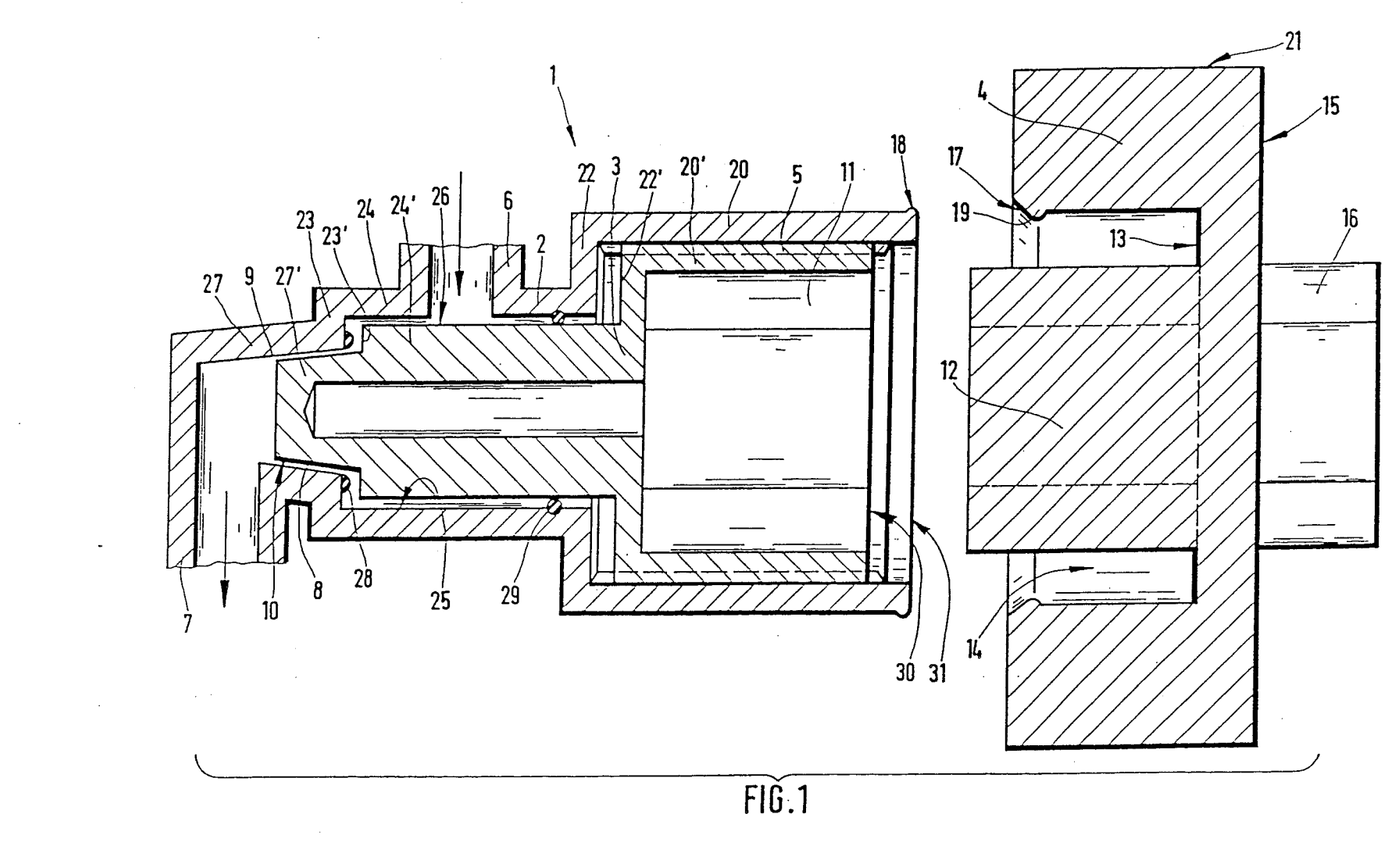
FIG. 1 is a sectional view of a first embodiment of the metering device according to the invention.

The first embodiment of the metering device or metering valve shown in FIG. 1 consists of an adjusting means 1 and an actuating member 4 for the adjusting means. The adjusting means 1 consists of a housing 2 and a body 3 supported and guided movably inside the same. The structure of the housing 2 is that of a valve housing and the structure of the body 3 that of a valve body. The housing 2 and the body 3 essentially are made like stepped, converging hollow cylinders and are disposed coaxially inside each other.

Sections 20, 24, and 27 of the housing 2 corresponding to three cylinder steps pass over into each other by sections 22 and 23. In corresponding manner the three sections 20', 24', and 27' of body 3 pass over into each other by sections 22' and 23'.

The body 3 is supported and guided for rotation in the housing 2 by way of a thread 5. The thread 5 is disposed in the first sections 20 and 20' of the housing 2 and of the body 3, respectively.

The second section 24 bordering on the first section 20 of the housing 2 is equipped with a connecting piece 6. The third section 27 of the housing 2 bordering on the second section 24 is equipped with another connecting piece 7. The two connecting pieces or nozzles thus are arranged offset with respect to each other in axial direction of the housing. They serve as tube connections for the introduction and discharge of liquids into and out of the metering device, such as plasma, antibiotics, etc. In the embodiment shown, the liquid flows through the connecting piece 6 into the intermediate space between the housing 2 and the body 3, exiting from the same through the connecting piece 7. The cross section of this connecting channel can be varied in a channel section, hereinafter referred to as flow passage 8. This flow passage 8 is defined by a conical surface 9 formed . the inner wall of housing section 27 and a conical surface 10 made correspondingly in the outer wall of the third body section 27'.

A hexagon socket 11 extending in axial direction is formed in the end portion 20' of body 3 remote from the flow passage 8. It is adapted for engagement with a complementary hexagon head 12 formed on the rotary knob 4. During mutual engagement of the two hexagons 11 and 12 the cross section of the flow passage 8 can be varied by turning the rotary knob 4.

The hexagon head 12 is arranged in the manner of a first axle journal centrally on the bottom 13 of a cylindrical recess 14 formed in the rotary knob 4. A chamfer 17 is formed at the free edge of the recess 14, the average diameter of the chamfer being greater than the diameter of a first annular bead 18 formed along the free edge of the housing 2. The chamfer 17 of the recess 14 is followed by a second annular bead 19. In nested condition of the adjusting means 1 and the rotary knob 4 the two beads 18 and 19 constitute a special stop.

A hexagon head 16 protrudes centrally like a second axle journal from the bottom surface 15 remote from the cylindrical recess 14 in the rotary knob 4, and it is likewise shaped for engagement with the hexagon socket 11. The cylindrical jacket surface of the rotary knob 4 finally is provided with rotary knob knurling 21 for ease of rotation of the knob.

A sealing ring 28 is positioned in the annular step 23 of the housing 2 for tight sealing of the connecting passage between the connecting pieces 6 and 7. An O-ring 29 disposed between the step 22 of the housing 2 and the connecting piece 6 prevents liquid escape in the direction of the first housing section 20.

In operating condition, the liquid to be infused into the body of a living being flows from the connecting piece 6 to the connecting 7. Axial shifting of the body 3 inside the housing 2 serves to vary the cross section of the conical, annular flow passage 8. To accomplish that, the hexagon socket 11 of the supporting body 3 and one of the two hexagon heads 12 or 16 of the rotary knob 7 are brought into effective engagement with each other and then the body 3 is twisted inside the housing 2 by means of the thread 5. This turning causes axial displacement of the body 3 in the housing 2 and this in turn leads to a change of the cross section of the flow passage 8 and thus to alteration of the flow rate through the same.

If hexagon 12 located in the recess 14 of the rotary knob 4 is to be made use of for changing the flow cross section, then the rotary knob 4 must be pushed on the first section 20 of the housing 2. The chamfer 17 at the outer edge of the rotary knob recess 14 and the use of elastically deformable material facilitate the slipping-on of the rotary knob 4 on the cylindrical housing section 20 with its bead 18 at the outer edge. The beads 18, 19 take care that the rotary knob 4 cannot slip unintentionally off the cylindrical housing section 20 and off the hexagon 11.

The rotary knob 4 is pulled off the adjusting means 1 composed of the housing 2 and the body 3 as a means of safeguarding against intentional or unintentional adjustment of the metering device That is permitted in spite of the axial abutment established by the beads 18 and 19 because the rotary knob 4 and/or the adjusting means 1 are deformable elastically. As the end face 31 of the body 3 does not protrude outwardly beyond the end face 30 of the housing 3, an unauthorized user of adjusting means 1 not disposing of rotary knob 4 cannot turn the body 3 to thereby change the flow passage 8. If, on the other hand, the authorized operator of the metering device briefly wishes to make a change in the flow rate, he will use the short hexagon head 16 at the rotary knob bottom 15 remote from the recess to actuate the body 3. Hereby the hexagon head 16 can be introduced especially quickly into the hexagon socket 11, as in a system of key and lock, and thus particularly quick operation of the metering device is rendered possible.

Figure 1A:
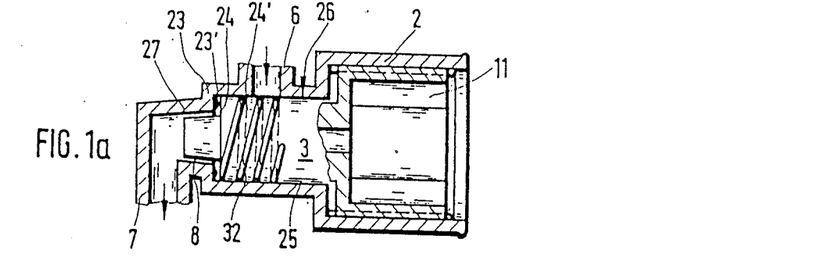
FIG. 1a is a view, partly in section, of a modified adjusting means according to FIG. 1, including a thread-like portion of the flow passage on the valve body.

In the case of the embodiment shown in FIG. 1a the body surface 26 of the second, i.e. central cylindrical body section 24' rests rotatably on the inner wall 25 of the housing in the central housing section 24 In this portion a thread-like flow passage 32 passes through the surface 26 of the body 3. The courses of thread forming the flow passage 32 are constant in cross section. With this embodiment the liquid flows through the connecting piece 6 across the thread-like flow passage 32 to the annular, conically tapering flow passage 8 and then out of the connecting piece 7 into the body of the living being.

If the rotary knob 4, not shown in this presentation, is turned, the body 3 is displaced in axial direction by the engagement between hexagon and counter-hexagon. This changes not only the cross section of flow passage 8 (explained already with reference to FIG. 1) but also the length of the groove-like flow passage 32 arranged like a thread. The number of courses of the thread located between the the connecting piece 6 and the flow passage 8 differs in response to the position of the body 3 with respect to the housing 2. A change in length of the flow passage 32 varies its flow resistance (increasing flow resistance at increasing length of the flow passage).

The embodiment shown in FIG. 1a is similar to the embodiment according to FIG. 1 with the exception of the central sections 24 and 24' of the housing 2 and of the body 3, respectively.

Figure 2A:
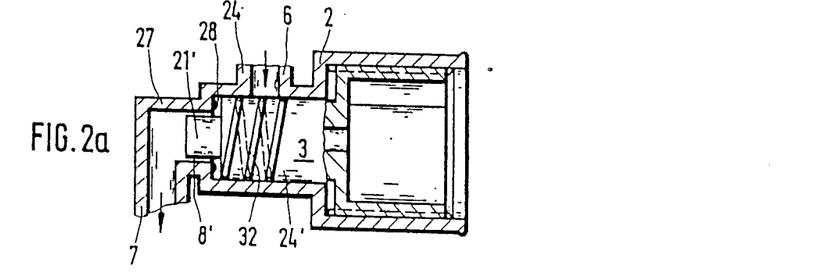
FIG. 2a is a view, partly in section, of a modified adjusting means as compared to FIG. 1a, including a cylindrical end portion of the valve body.

The embodiment according to FIG. 2a differs from the embodiment illustrated in FIG. 1a substantially by the following features:

The third sections 27 and 27' of the housing 2 and body 3, respectively, are not conical but instead cylindrical in shape.

Accordingly, the cross section of the flow passage 8' does not change upon axial shifting of the body 3. With this embodiment, therefore, the flow passage 8' always has a constant cross section. The flow resistance of the overall flow channel, i.e. of flow passages 8 and 32 thus is altered only by varying the length thereof.

The manufacturing technique of the housing 2 and body 3 is simplified by the cylindrical design of the two third sections 27, 27'. Furthermore, it is advantageous that an O-ring seal between the outer wall of the central body section 24' and the central housing section 24 is not required in principle.

Another advantage which should be mentioned is the more precise supporting of the body 3 in the housing 2, as compared to FIG. 1. The body 3 is guided in the housing 2 not only by the thread 5 but also by its central section 24'. These advantages, by the way, apply also to the embodiment according to FIG. 1a.

Figure 2B:
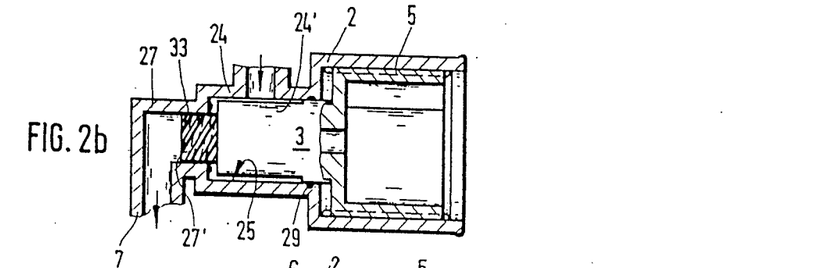
FIG. 2b is a view, partly in section, of a modified adjusting means as compared to FIG. 2a, including a thread-like extension of the flow passage in the cylindrical end portion of the valve body.

FIG. 2b shows an embodiment similar to the one of FIG. 2a. Here the thread-like flow passage 33 is not located in the central cylindrical section 24 of the body 3, as is the case in FIG. 2a, for instance, but instead in the third cylindrical section 27. The central, i.e. the second cylindrical section 24' of the body 3 has a smaller diameter than the diameter of the inner wall 25 of the housing As with FIG. 1, an O-ring is provided against any escape of the liquid in the direction of the thread 5.

The especially precise support and guidance of the body 3 in the housing 2 is an advantage of this embodiment This means that unintentional adjustment of the body 3 with respect to the housing 2 largely can be avoided even if the metering device suffers vibrations. The flow resistance is varied merely by changing the flow passage 30 with this embodiment.

Figure 2C:
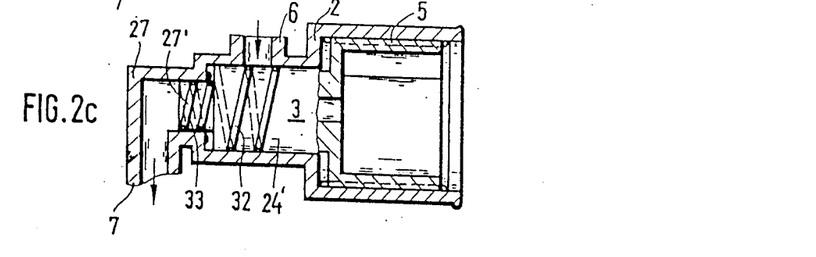
FIG. 2c is a view, partly in section, of an adjusting means modified as compared to FIGS. 2a and 2b and including a thread-like flow passage both in the cylindrical end portion and in the central portion of the valve body.

The principles of FIGS. 2a and 2b are realized in common in FIG. 2c. A thread-like flow passage 32, 33 is located in the second as well as in the third cylindrical sections 24' and 27' of the body 3.

If—contrary to FIG. 1—the length of hexagon 12 is less than the depth of the surrounding recess 14, then the free end surface thereof is largely protected from becoming damaged.

Fundamentally, the thread-like flow passages may be formed also in the inner wall of the second and/or third sections 24 and 27 of the housing 2 rather than in the corresponding outer wall sections of the body 3. Instead, they may also be formed as a common thread for the housing 2 and the body 3, especially in the form of a trapezoidal thread. This embodiment has the advantage that the thread-like flow passage, at the same time, may serve as screw thread for guiding and shifting the body 3 inside the housing 2 so that the thread 5 may be dispensed with in principle.

Figures 3, 6, 7, 8:
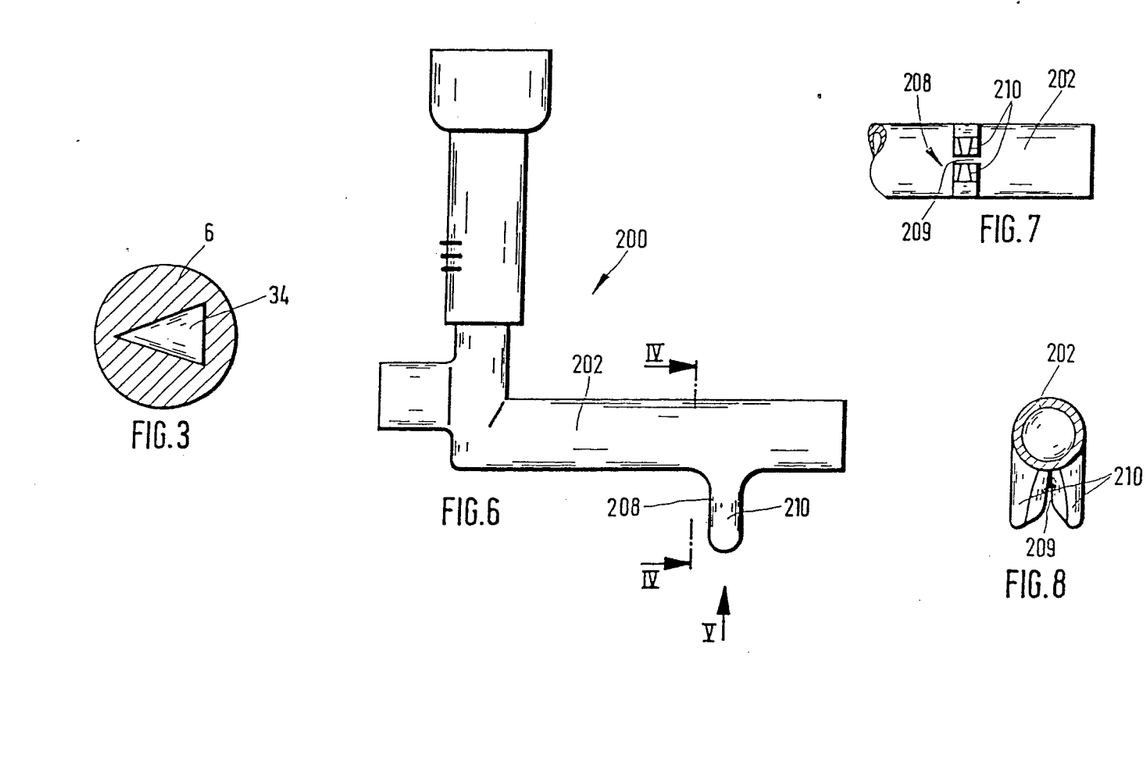
FIG. 3 shows a triangular inner cross section of the connecting piece.
FIG. 6 is a view of a housing according to another embodiment of the invention, including an integrally molded hose clamp.
FIG. 7 shows the section IV—IV of FIG. 6.
FIG. 8 shows section V of FIG. 6.

FIG. 3 presents a particularly advantageous embodiment of the connecting piece 6 which is shown in cross section. The inner cross section 34 of the connecting piece 6 tapers towards the third section 27 of the housing 2. As shown, preferably the configuration of the inner cross section is that of a triangle, an isosceles triangle being especially preferred. This triangular inside cross sectional shape 34 of the connecting piece 6 extends through the wall of the second section 24 all the way into the inlet of the intermediate space between the housing 2 and the body 3.

This type of design of the inner cross section 34 of the connecting piece 6 provides another possibility of controlling the rate of flow through the metering device, namely in response to the positioning of the body 3 with a step 23' opposite the triangular area in the housing 2. In particular this permits fine control in the range of fine flow rates and quick control in the range of high flow rates.

In principle, it is sufficient to provide the inner cross section 34 described above in the area of the mouth only, i.e. in the end portion of the channel 6 located directly opposite the body 3.

The metering valve shown in FIGS. 4 to 8 comprises three main components:
a valve housing 200
a valve body 300, and
an actuating member 400.

Figures 4, 5:
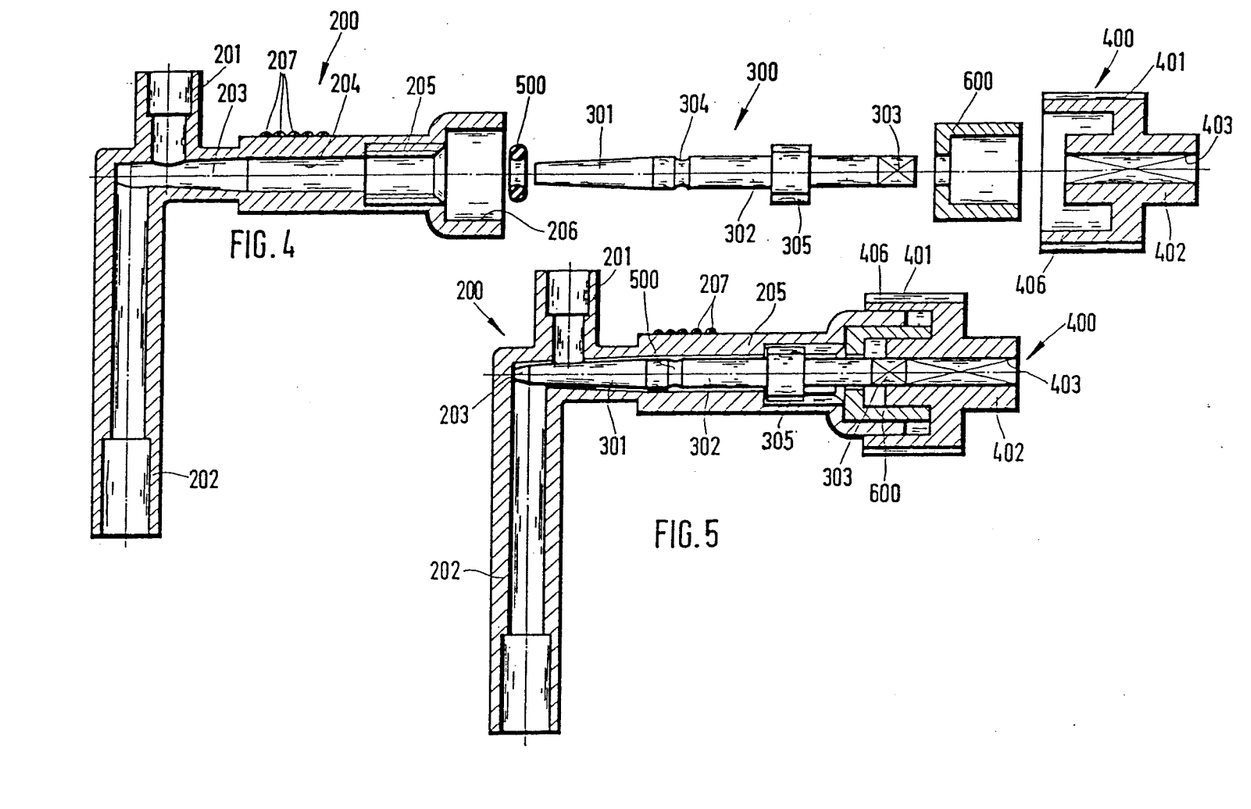
FIG. 4 is a cross sectional and exploded view of the metering valve according to the invention.
FIG. 5 shows the metering valve according to FIG. 4 in cross section upon mounting thereof.

Moreover, a sealing ring 500 and a bearing bush or sleeve 600 are provided.

The valve housing 200 comprises connecting pieces in the form of an inlet nozzle 201 and an outlet nozzle 202, both being disposed paraxially, yet offset with respect to each other. The outlet nozzle 202 is much longer than the inlet nozzle 201 and has such dimensions that it can be grasped and held by the middle finger, the ring finger, and the little finger of the hand of an operator.

Both the inwardly located end of the inlet nozzle 201 and the inwardly disposed end of the outlet nozzle 202 open in offset, opposed relationship into a valve chamber 203 the central axis of which intersects the central axis of the two connecting pieces 201, 202, extending perpendicularly with respect to the same.

The valve chamber 203 is of conical design, tapering from the mouth of the inlet nozzle 201 towards the entry into the outlet nozzle 202. At its converging end, the valve chamber does not extend beyond the outlet nozzle 202. Yet its other flaring end extends beyond the mouth of the inlet nozzle 201 and thereafter merges into a cylindrical section 204 of a length which corresponds to that of the converging conical section At its end remote from the valve chamber 203, the cylindrical section 204 passes over into a threaded section 205 formed with an internal thread. The smallest diameter of the internal thread is greater than that of the cylindrical section 204.

A circular cylindrical receiving section 206 borders on the end of the threaded section 205 remote from the cylindrical section 204. The diameter of this section 206 is much greater than that of the threaded section 205.

The length of the valve chamber 203, the cylindrical section 204, the threaded section 205, and the receiving section 206 each are matched with the dimensions of the valve body 300. The dimensional correlation is illustrated in FIG. 5 which shows these elements.

The valve body 300 is embodied by an elongated pin having a conical portion at its end, namely end section 301 followed by a circular cylindrical section 302. The end section 301 is of complementary conical shape with respect to the valve chamber 203. The thicker end of the conical end section 301 forms a flush transition with the cylindrical section 302, the latter having a hexagon 303 formed at its free end.

Near the conical section 301, the cylindrical section 302 is formed with an annular groove 304 to take up the sealing ring 500. When in effective position, the outer circumference of the sealing ring is in sealing engagement with the inner peripheral wall of the cylindrical section 204 of the valve housing 200.

Approximately in the middle between the annular groove 304 and the hexagonal end 303, the circular cylindrical section 302 includes a section 305 having an enlarged outer diameter and being formed with an external thread. This external thread matches the thread of the threaded section 205 of the valve housing 200. The threaded sections 205, 305 are located such that the conical section 301 of valve body 300 just comes to lie in sealing engagement against the inner wall of the valve chamber 203 when the two threaded sections 205, 305 are fully screwed into each other, in other words when the two ends of the threaded sections 205, 305 facing the conical valve chamber abut against each other. It may likewise be advantageous if the conical section 301 of the valve body still is at a minor capillary distance from the inner wall of the valve chamber when the threaded sections 205 and 305 are fully screwed into each other. In this manner bursting of the wall of the valve chamber 203 can be prevented in case the valve body 300 is entered too deeply.

The bearing bush or sleeve 600 is pushed over the pin-like end 303 of the valve body 300. It is designed as a cylindrical sleeve having an inner flange at the end. The inner flange in turn is formed with a central bore, big enough to permit passage of the pin-like end 303 of the valve body 300 but dimensioned such that the threaded section 305 of the valve body 300, in its one end position, abuts against the inner flange of the bearing sleeve 600. Preferably the inner diameter of the central bore of the inner flange and the outer diameter of the cylindrical section 302 are matched such that they form a germ barrier during their relative coaxial displacement in the area of their mutual contact. Usually a snug fit of these two parts is sufficient to accomplish that.

At its outside the bearing sleeve 600 is designed so as to match the receiving section 206 inside of which it is bonded.

The actuating member 400 essentially is made up of two sleeves arranged concentrically inside each other, namely one circular cylindrical outer sleeve 406 and one inner sleeve 402. The outer sleeve 406 carries a knurling 401 on the outside. The inner diameter of the outer sleeve 406 is dimensioned such that it is a clearance fit on the outer circumference of the receiving section 206.

An inner flange carrying the inner sleeve 402 is arranged at one end of the receiving sleeve 406. The inner sleeve protrudes from both ends of the inner flange and includes a hexagon socket 403 which fits on the hexagon head 303. The outer diameter of the inner sleeve 402 is such that it can enter into guiding sliding engagement with the inner diameter of the bearing sleeve 600. Thus, when hexagon socket 403 is slipped on the hexagon head 303 of the valve body 300, the actuating member 400 is supported in guided fashion for rotational movement.

The material of the bearing sleeve 600 has a low coefficient of friction with respect to that of the inner sleeve 402.

Moreover, the actuating member 400 is made of plastic material which preferably is dyed so that it will strike the eye when a patient's infusion installation is checked in passing. Therefore, it can be noticed at once and remedied if this actuating member 400 accidentally should have remained on the metering valve.

The valve housing 200 preferably is made of a clear transparent, colorless material, such as acrylic glass.

The sealing ring 500 preferably is given a striking color so that its position and thus the position of the valve body 300 inside the valve housing 200 can be recognized at first glance.

A graduation 207 for preadjustment is formed on the valve housing 200 opposite the sealing ring 500

The inlet nozzle 202 which faces downwards upon assembly may serve not only to be held by the last three fingers of the operating hand during operation of the slipped on actuating member 400 by the thumb and forefinger of that hand. It is also possible to utilize this outlet nozzle 202 as a propping means acting as the torque support of an adjusting drive means or servo motor. In this event the drive means, having a fork-like member, may embrace the outlet nozzle 202 from both sides. It may also be mounted stationarily at a separate location and be connected to the valve body 300, for example, by a flexible shaft. In that event a separate torque support is provided, for instance in the form of a weight attached to the outlet nozzle 202, and it engages the metering valve. Finally, it is likewise possible to provide a torque support especially designed to match a setting motor, and to provide the same in addition to a member which constitutes a handle or instead of any such member.

FIG. 6 shows the valve housing 200 of a different embodiment of the metering valve: other than with the embodiment of FIGS. 4 and 5, this valve housing includes a tube or hose clamp 208 in addition which is formed integrally with the outlet nozzle 202 designed as handle and is provided at the side remote from the actuating member 400 (not shown in FIG. 6). It may be gathered especially well from FIG. 7 that the hose clamp is formed of two clamping legs 201 both extending parallel to each other and perpendicularly with respect to the outlet nozzle 202, their outer surfaces forming a flush transition with the outer circumference of the outlet nozzle 202.

A clamping slot 209 is formed between the two clamping legs 210, and the width thereof is dimensioned such that a tube (not shown) connected to the end of the outlet nozzle 202 and laid in a loop, when introduced into the slot, is squeezed so as to be shutoff reliably.

The outer ends of the clamping legs 210 are rounded in order to avoid damaging the tube in any way.

As illustrated specifically in FIG. 8, the clamping legs 210 are chamfered toward the clamping slot 209, forming only a narrow clamping spot and yet facilitating the insertion of the tube into the clamping slot 209.

Furthermore, as shown in FIG. 7, the free ends of the clamping legs 210 are chamfered at their free ends toward the clamping slot 209. This chamfering, on the one hand, facilitates the introduction of the tube into the clamping slot and, on the other hand, it offers a seat for the tube. Thus the tube may be attached to the outlet nozzle, for example, by a bandage such that it will pass through the chamfering to be gathered from FIG. 4 and remain in permanent abutment against the same. If the medicine supply to the patient is to be interrupted quickly, it suffices to press the tube quickly into the clamping slot 209 by the fingers or the palm of the hand which grips around the outlet nozzle 202. In this way, for instance, the administration of a drug can be interrupted much more rapidly than can be done by readjustment of the actuating member 400 for example.

All that has to be done for release of the tube from the clamping slot is to introduce the finger tip between the tube and the adjacent outside surface of the outlet nozzle 202, thereby lifting the tube out of the clamping slot 209.

What is claimed is:

1. A metering device for adjusting a flow rate of a liquid to be infused into or taken out from the body of a living being, comprising:

adjusting means including an inlet means for admitting liquid into the metering device and outlet means for discharging liquid from the metering device, and two adjusting members defining therebetween a flow passage from said inlet means to said outlet means, one of said adjusting member being rotatable relative to another adjusting member to adjust a flow resistance of said flow passage and thus the flow rate of the liquid passing therethrough;

actuating means disengageably-engageable with said adjusting means to induce rotation of said one adjusting member relative to another; and locking means provided on said actuating means and said adjusting means and adapted to effect engagement of said actuating means with said adjusting means and connect them to each other in a keylocking manner, said locking means being constructed so that said actuating means can be disengaged from said adjusting means in any adjusted position of said adjusting means to thereby avoid unintentional or erroneous adjustment of said two adjusting members relative to each other.

2. A metering device as defined in claim 1, wherein said locking means include a hexagonal recess provided in said one adjusting member and at least one hexagonal head provided on said actuating means and mating with an engageable in said recess.

3. A metering device as defined in claim 2, wherein said actuating means include an actuating member having two hexagonal heads provided at two sides thereof and each being engageable in said recess.

4. A metering device as defined in claim 3, and further comprising shutoff means connected downstream of said adjusting means and including a hose clamp formed integrally with said adjusting means in a common housing means.

5. A metering device as defined in claim 4, wherein said hose clamp includes two clamping legs forming therebetween a clamping slot, said clamp being formed integrally with a handle provided on the metering device.

6. A metering device as define din claim 1, wherein said inlet means are offset relative to said outlet means in an axial direction of said adjusting means.

7. A metering device as defined in claim 1, wherein one of said adjusting member is a housing designed as a valve housing and another of said adjusting members is a body designed as a valve body and guided for displacement in said housing to vary the flow resistance, said body being adapted to be engaged at its end portion remote from the flow passage with an actuating member of said actuating means.

8. A metering device as defined in claim 7, wherein said body is guided int he housing by a thread, and the actuating member is constructed as a rotary knob.

9. A metering device as defined in claim 8, wherein said body is arranged coaxially inside said housing, said inlet means being axially offset relative to said outlet means, said body being mounted in said housing so that within a range of said offset the flow resistance is variable by changing a cross section and a length of the flow passage.

10. A metering device as defined in claim 9, wherein said housing and said body have complementary conical surfaces which define the cross section of the flow passage and a spacing between said conical surfaces being variable by axial displacement of the body in said housing at said thread.

11. A metering device as defined in claim 7, further including a handle for an operator and providing a support connected to the valve housing to accommodate forces of reaction and torques occurring upon operation of the actuating member.

12. A metering device as defined in claim 1, wherein said locking means include a hexagonal recess provided in said actuating means and a hexagonal head provided on said one adjusting member and mating with and engageable in said recess.

13. A metering device as defined in claim 12, wherein said first and second adjusting members are formed as a valve housing and a valve body, respectively, said valve body being an elongated pin, said actuating means including an actuating member having said hexagonal recess, said elongated pin having an external thread, said valve housing having an internal thread complementary with said external thread, said pin terminating with said hexagonal head engageable in said recess of said actuating member.

* * * * *